(12) United States Patent
Skufca

(10) Patent No.: US 11,266,569 B2
(45) Date of Patent: Mar. 8, 2022

(54) PRIMARY PACKAGING FOR STORAGE AND ADMINISTRATION OF MEDICAL AND PHARMACEUTICAL COMPOUNDS

(71) Applicant: Peter Skufca, Stockach Bodensee (DE)

(72) Inventor: Peter Skufca, Stockach Bodensee (DE)

(*) Notice: Subject to any disclaimer, the term of this patent is extended or adjusted under 35 U.S.C. 154(b) by 640 days.

(21) Appl. No.: 16/141,978

(22) Filed: Sep. 26, 2018

(65) Prior Publication Data
US 2019/0021949 A1 Jan. 24, 2019

Related U.S. Application Data

(63) Continuation of application No. 14/745,440, filed on Jun. 21, 2015, now abandoned, which is a
(Continued)

(30) Foreign Application Priority Data

Dec. 21, 2012 (WO) .................. PCT/EP2012/076601

(51) Int. Cl.
*A61J 1/14* (2006.01)
*A61J 1/06* (2006.01)
(Continued)

(52) U.S. Cl.
CPC ............ *A61J 1/1481* (2015.05); *A61J 1/062* (2013.01); *A61J 1/2006* (2015.05); *A61J 1/2013* (2015.05);
(Continued)

(58) Field of Classification Search
CPC .................. A61M 5/2429; A61M 5/24; A61M 2005/2407; A61M 5/283; A61M 5/2455; A61J 1/2013; A61J 1/2096; A61J 1/062
See application file for complete search history.

(56) References Cited

U.S. PATENT DOCUMENTS 1,817,033 A 8/1931 Graver .......................... 604/203
2,408,323 A 9/1946 Lockhart ....................... 604/198
(Continued)

FOREIGN PATENT DOCUMENTS

DE 1207043 B 4/1962
DE 3924830 A1 7/1989
(Continued)

OTHER PUBLICATIONS

English translation of the Feb. 20, 2020 Office action from the Japanese Patent Office in the related foreign application JP2019-066598. (3 pages).
(Continued)

*Primary Examiner* — Adam Marcetich
(74) *Attorney, Agent, or Firm* — Imperium Patent Works; Darien K. Wallace (57) ABSTRACT

A primary packaging for storage and/or administration of medical or pharmaceutical compounds includes a container that has a predetermined filling volume for receiving a medical or pharmaceutical compound. The container is permanently closed at a first end and has an integrally formed, circumferential flange portion at an open second end. The container has a cylindrical barrel that extends between the first end and the flange portion such that the barrel has an inner diameter and outer diameter corresponding to that of a standardized syringe for a nominal volume of the standardized syringe corresponding to the predetermined filling volume. Furthermore, a cross-sectional shape of the flange portion corresponds to the cross-sectional shape of a flange of a standardized vial. The primary packaging also includes a closure element that is adapted to fit tightly on the flange portion and into the barrel for sealing the open second end of the container.

20 Claims, 5 Drawing Sheets

Related U.S. Application Data continuation of application No. PCT/EP2012/076601, filed on Dec. 21, 2012.

(51) Int. Cl.

| | | |
|---|---|---|
| *A61M 5/24* | (2006.01) | |
| *A61J 1/20* | (2006.01) | |
| *B65B 7/28* | (2006.01) | |
| *B65B 1/28* | (2006.01) | |
| *B65D 51/00* | (2006.01) | |

(52) U.S. Cl.
CPC ............ *A61M 5/24* (2013.01); *A61M 5/2455* (2013.01); *B65B 7/2821* (2013.01); *B65D 51/002* (2013.01)

(56) References Cited

U.S. PATENT DOCUMENTS

| | | | | |
|---|---|---|---|---|
| 3,071,274 A | | 1/1963 | Ravn ............................... | 215/37 |
| 3,413,975 A | | 12/1968 | Hein .............................. | 128/253 |
| 3,580,251 A | | 5/1971 | Guiriec ........................... | 128/220 |
| 3,584,626 A | * | 6/1971 | Johansson ............... | A61M 5/31 604/193 |
| 3,994,296 A | * | 11/1976 | Cloyd ................ | A61M 5/2429 604/203 |
| 4,568,336 A | | 2/1986 | Cooper .......................... | 604/240 |
| 4,692,156 A | * | 9/1987 | Haller ................... | A61M 5/322 600/576 |
| 4,932,941 A | * | 6/1990 | Min .................... | A61M 5/5013 604/110 |
| 4,969,877 A | * | 11/1990 | Kornberg ............. | A61M 5/322 604/195 |
| 5,352,196 A | | 10/1994 | Haber et al. ...................... | 604/90 |
| 5,380,297 A | * | 1/1995 | Wadman ............. | A61M 5/2429 604/195 |
| 5,407,436 A | | 4/1995 | Toft et al. ...................... | 604/411 |
| 5,478,324 A | | 12/1995 | Meyer ............................ | 604/203 |
| 5,536,253 A | * | 7/1996 | Haber ................... | A61M 5/322 604/110 |
| 5,833,660 A | * | 11/1998 | Nathan ............... | A61M 5/5013 604/110 |
| 6,007,520 A | | 12/1999 | Sudo ............................ | 264/496 |
| 6,039,713 A | | 3/2000 | Botich .......................... | 604/110 |
| 6,123,688 A | | 9/2000 | Botich et al. ................. | 604/110 |
| 6,565,529 B1 | * | 5/2003 | Kimber ............... | A61M 5/3135 604/110 |
| 2003/0163092 A1 | * | 8/2003 | Parker .................. | A61M 5/326 604/198 |
| 2004/0111063 A1 | | 6/2004 | Botich et al. ................. | 604/195 |
| 2004/0127859 A1 | * | 7/2004 | Ward .................... | A61M 5/5013 604/222 |
| 2005/0137533 A1 | * | 6/2005 | Sudo .................. | A61M 5/31511 604/218 |
| 2006/0089601 A1 | | 4/2006 | Dionigi ......................... | 604/181 |
| 2006/0111671 A1 | * | 5/2006 | Klippenstein ....... | A61M 5/3293 604/110 |
| 2006/0168916 A1 | | 8/2006 | Griebel et al. .................. | 53/489 |
| 2007/0225656 A1 | | 9/2007 | Hoyle, Jr. ..................... | 604/207 |
| 2008/0221529 A1 | * | 9/2008 | Kiehne ............... | A61M 5/3234 604/211 |
| 2009/0259195 A1 | | 10/2009 | Lin Lee ........................ | 604/195 |
| 2010/0114058 A1 | | 5/2010 | Weitzel et al. ............... | 604/411 |
| 2010/0331778 A1 | * | 12/2010 | Wayman ............... | A61M 5/502 604/110 |
| 2011/0009830 A1 | * | 1/2011 | Kosinski ............ | A61M 5/31511 604/227 |
| 2011/0022023 A1 | * | 1/2011 | Weitzel ................ | A61J 1/1412 604/414 |
| 2012/0088714 A1 | * | 4/2012 | Kumar ..................... | A61J 1/14 514/1.1 |

FOREIGN PATENT DOCUMENTS

| | | |
|---|---|---|
| DE | 19652708 A1 | 12/1996 |
| DE | 10121232 C2 | 4/2001 |
| DE | 10340613 A1 | 8/2003 |
| EP | 0298585 | 5/1988 |
| EP | 0312035 A2 | 10/1988 |
| EP | 0510683 B1 | 4/1992 |
| EP | 0707859 A1 | 6/1995 |
| EP | 2535073 A1 | 6/2011 |
| JP | 58-126840 | 2/1982 |
| JP | 4-327836 | 4/1991 |
| JP | 8-506749 | 8/1995 |

OTHER PUBLICATIONS

International search report dated Sep. 11, 2013, from the European Patent Office in the parent international application PCT/EP2012/076601 (15 pages).

International Organization for Standardization ISO 8362-1 standard for injection containers and accessories Part 1, third edition Dec. 15, 2009 [ISO 8362-1:2009(E)] (10 pages).

International Organization for Standardization ISO 8362-2 standard for injection containers and accessories Part 2, second edition Oct. 15, 2008 [ISO 8362-2:2008(E)] (10 pages).

International Organization for Standardization ISO 11040-4 standard for prefilled syringes Part 4, 2nd edition Feb. 1, 2007 [ISO 11040-4:2007 (E)] (14 pages).

International Organization for Standardization ISO 11040-5 standard for prefilled syringes Part 5, 3rd edition Jan. 15, 2012 [ISO 11040-5:2012 (E)] (10 pages).

Office action dated Oct. 11, 2016 from the Japanese Patent Office in the related foreign application JP2015-548226 and English translation (7 pages).

Office action dated May 8, 2018 from the Japanese Patent Office in the related foreign application JP2015-548226 and English translation (6 pages).

English translation of an Office action from the Mexican Patent Office in the related foreign application MX/a/2015/007910 (3 pages).

\* cited by examiner

PRIMARY PACKAGING FOR STORAGE AND ADMINISTRATION OF MEDICAL AND PHARMACEUTICAL COMPOUNDS

CROSS REFERENCE TO RELATED APPLICATION

This application is a continuation of, and claims priority under 35 U.S.C. § 120 from, nonprovisional U.S. patent application Ser. No. 14/745,440 entitled "Primary Packaging for Storage and Administration of Medical and Pharmaceutical Compounds," filed on Jun. 21, 2015. Application Ser. No. 14/745,440 in turn is a continuation-in-part of, and claims priority under 35 U.S.C. § 120 and § 365(c) from International Application No. PCT/EP2012/076601, filed on Dec. 21, 2012, and published as WO 2014/026721 A2 on Feb. 20, 2014. The subject matter of each of the foregoing documents is incorporated herein by reference.

TECHNICAL FIELD

The invention relates to primary packaging for storage and/or administration of medical or pharmaceutical compounds.

BACKGROUND

Various types of primary packaging for storage and/or administration of medical or pharmaceutical compounds are known in the prior art that are intended to contain and protect those compounds and that are or can be in direct contact with the compounds. According to the "Guidelines on packaging for pharmaceutical Products" issued in the Technical Report Series No. 902, 2002, by the World Health Organization (WHO), such primary packaging must protect the pharmaceutical or medical products against all adverse external influences that may affect its quality or potency such as, for example, light, moisture, oxygen, biological contamination and mechanical damage. In particular, such primary packaging must not interact physically or chemically with the contained medical or pharmaceutical compounds in any way that would alter their quality.

The primary packaging for the intended use usually includes a container that holds or is intended to contain and protect medical or pharmaceutical compounds, and a closure that covers the compounds or which is intended to seal the container. These containers and closures may be intended for single-use or multi-use. According to the above-mentioned WHO guidelines, the primary packaging must protect the contents from extraneous matter, from loss of the substance, and from efflorescence, deliquescence and evaporation under normal conditions of handling, shipping and storage.

For use as primary packaging, several containers are well known in the prior art. Containers that are often used for the purpose of packaging medical or pharmaceutical compounds are, for example, vials, ampoules, cartridges, bottles or (pre-filled) syringes. These containers may be manufactured from glass or plastic. Of particular importance in such usage are ampoules that are single-use containers sealed by fusion and to be opened exclusively by breaking, vials that are single-use or multi-use containers closed by a stopper and/or an overseal, and syringes that are cylindrical devices with a cannula-like nozzle and with or without a fixed needle and a movable piston. Furthermore, for use as primary packaging, several types of closures are known in the prior art. For example, such a closure may be made from elastomeric materials and from polyethylene or polypropylene. In this context, it is notable that such closures usually come in different shapes and sizes, e.g., stoppers for infusion or injection bottles or plungers for prefilled syringes, depending on the type of container.

Those containers and closures are specified, inter alia, by the standards on packaging issued by the International Organization for Standardization (ISO). In particular, the relevant ISO standards are ISO 8362-1, 8362-2, ISO 11040-4 and ISO 11040-5.

The choice for assembling the primary packaging depends, among other things, on the one hand on the degree of protection required as well as on the compatibility with the contents, and on the other hand the filling method, the production costs, the presentation or the form of administration format as well as the convenience of the packaging for the user, e.g., the size, weight and method of opening. Regarding the filling method, it is notable that facility for filling is usually laid out for only one type of packaging. For example, a vial can only be filled in a vial-filling facility, and a syringe can only be filled in a syringe-filling facility.

Furthermore, it is known that the individual components of such packaging, including the container and the closure, and also the combination thereof, must pass through a variety of tests to be approved or certificated as the primary packaging. Such tests are complex and costly. Therefore, the primary packaging for a specific medical or pharmaceutical compound is often set or fixed in the early-stage development of the compound and is changed in the further course of development only if necessary. Accordingly, a disadvantage of conventional primary packaging according to the prior art is its inflexibility with regard to a change of its structure, specific form of administration, etc. and/or of its individual components during development.

It is also known that, vaccines filled in pre-filled syringes, for example, are produced only seasonally as their typical vaccination application is carried out only in certain seasons. Nevertheless, the filling facilities and filling lines for the syringes must be kept throughout the year because they cannot be dismantled easily and built up again. Consequently, the maintenance costs for the filling facilities used for filling syringes are high or the facilities they are shut down for a period of time during the year. This has a negative impact on the production costs of medical or pharmaceutical products.

It would therefore be desirable to provide a more flexible primary packaging that overcomes such drawbacks. For this purpose, several solutions have been proposed in the prior art. For example, European application EP0298585A1 describes a pre-filled syringe that is based on the use of a vial containing a medical compound in order to be able to fill the vial by using a conventional filling facility and technique for vials. The vial has an open bottom that is closed by a piston that can be coupled with a plunger. The system can be converted into a pre-filled syringe using an adapter cap having an internal needle and an external connection for a needle that is placed over a closure of the vial. A disadvantage of this system is that the vial can only be filled by using filling facilities used for filling vials. Moreover, due to the open bottom of the vial, the vial can only be used in connection with the proposed system.

The U.S. Pat. No. 4,568,336 describes another pre-filled syringe that has a tubular barrel that can be filled at either end. Both ends of the syringe barrel can be sealed with standard vial closures and crimped aluminum seals. One closure means for the barrel is a piston and the other closure means is adapted to receive a needle. A disadvantage of the proposed syringe is that it can only be used as a pre-filled syringe.

Therefore, it is an object of the present invention to improve the primary packaging for medical and pharmaceutical compounds with respect to cost, the structural means used and the flexibility of production.

SUMMARY

A primary packaging for storage and administration of medical and pharmaceutical compounds includes a container that has a predetermined filling volume for receiving a medical or pharmaceutical compound. The container is permanently closed at a first end and has an integrally formed, circumferential flange portion at an open second end. The container has a cylindrical barrel that extends between the first end and the flange portion such that the barrel has an inner diameter and outer diameter corresponding to that of a standardized syringe for a nominal volume of the standardized syringe corresponding to the predetermined filling volume. Furthermore, a cross-sectional shape of the flange portion corresponds to the cross-sectional shape of a flange of a standardized vial. The primary packaging also includes a closure element that is adapted to fit tightly on the flange portion and into the barrel for sealing the open second end of the container.

The primary packaging device for medical and pharmaceutical compounds includes a container, a closure element and an aluminum cap. The container has a cylindrical barrel, a permanently closed first end and an open second end. A circumferential flange portion is integrally formed around the open second end and extends radially from the open second end. The closure element has a fitting portion and a support portion. The fitting portion fits tightly into the open second end, and the support portion seals the open second end by contacting an upper surface of the flange portion. The aluminum cap has a central opening and surrounds the closure element and the flange portion of the container.

In one embodiment, the primary packaging includes a plastics element that is releasably fitted over the aluminum cap so as to provide access to the closure element through the central opening when the plastics element is flipped off. In another embodiment, the plastics element includes a gripping portion that passes through the central opening of the aluminum cap and extends axially upwards. The aluminum cap includes a breaking point located where the aluminum cap engages the flange portion of the container. The plastics element can easily be removed by folding the gripping portion such that the aluminum cap rips at the circumferentially extending breaking point.

In yet another embodiment, the primary packaging includes a container, a closure element and a needle extraction system with a plunger rod. A cannula extends axially through the plunger rod and protrudes out of both axial ends of the plunger rod. The container has a cylindrical barrel, a permanently closed first end and an open second end. A circumferential flange portion is integrally formed into the open second end and extends radially from the open second end. The closure element fits tightly into the open second end and has a threaded attachment means. A first end of the plunger rod can be screwed into the threaded attachment means.

In one aspect, the needle extraction system has a cylindrical tube section that extends substantially coaxially with the plunger rod, which is attached inside the cylindrical tube section. The plunger rod has an outer diameter that is smaller than the inner diameter of the barrel, and the cylindrical tube section has an inner diameter that is larger than the outer diameter of the barrel. The plunger rod slides inside the barrel while the cylindrical tube section slides down around the outside of the barrel.

A method of making a primary packaging device for medical and pharmaceutical compounds involves fitting a plunger stopper into a container and screwing a plunger rod into a hole in the plunger stopper. The container has a barrel, a permanently closed second end and a circumferential flange portion formed around a first open end. The outer diameter of the plunger rod is smaller than the inner diameter of the barrel. The plunger stopper has a female threaded hole with a thin bottom portion between the female threaded hole and the bottom side of the plunger stopper. The plunger stopper is fit tightly into the first open end of the container. Then a male threaded end of the plunger rod is partially screwed into the female threaded hole. A cannula extends axially through the plunger rod and protrudes through both the male threaded end and the top axial end of the plunger rod. The thin bottom portion of the plunger stopper is not penetrated by the cannula that protrudes from the male threaded end of the plunger rod.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings. In the description and claims, terms such as "upper", "lower", "top", "bottom", "up", "down", "upwards" and "downwards" are used to describe relative directions and orientations between different parts of the packaging, and it is to be understood that the overall structure being described can actually be oriented in any way in three-dimensional space.

Figure 1:
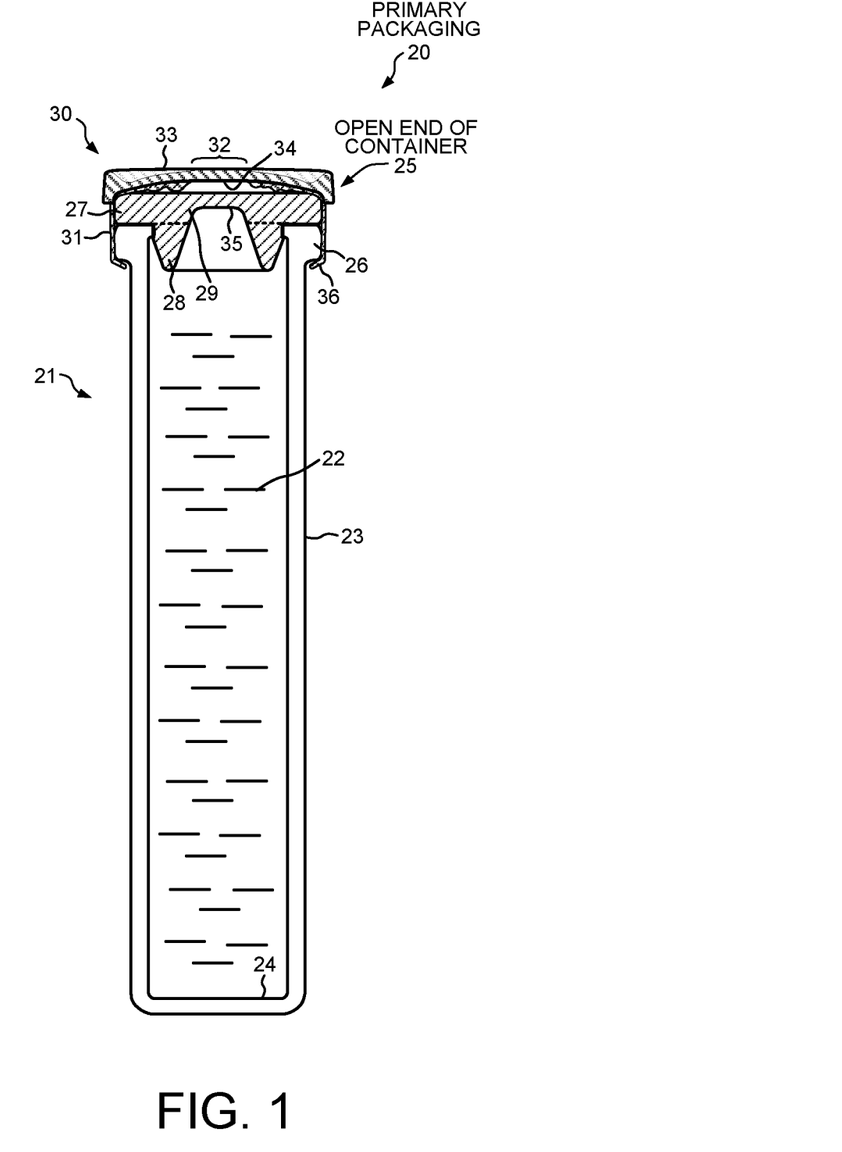
FIG. 1 is a schematized cross-sectional side view of a container with a closure element and a seal according to an embodiment of the invention.

FIG. 1 shows primary packaging 20 that includes a container 21 containing medical or pharmaceutical compounds 22. The cylindrical barrel 23 of the container 21 is permanently closed at the bottom end 24 and is open at the top end 25. A circumferential flange portion 26 extends radially outwardly from the barrel 23 at the top end 25. The primary packaging 20 for storage and/or administration of medical or pharmaceutical compounds 22 includes a container 21 having a predetermined filling volume for receiving a medical or pharmaceutical compound. The container 21 is permanently closed at a first end 24 and has an integrally formed, radially extending circumferential flange portion 26 at an open second end 25. The container 21 has a cylindrical barrel 23 that extends between the first end 24 and the flange portion 26. The primary packaging 20 also includes a closure element 27 which is preferably adapted to fit tightly on the flange portion 26 and/or to fit tightly into the barrel 23 in order to seal the open second end 25 of the container 21 (after filling of the container 21).

As described above, for the purpose of the disclosure, "primary packaging" is taken to mean any packaging that is in direct physical contact with the medical or pharmaceutical compound to be filled. Furthermore, the term "container" is used as a generic term for a container that is made of materials, such as glass and plastic, suitable for medical or pharmaceutical compounds. Preferably, a "cylindrical barrel" is to be understood as a hollow cylindrical barrel that is formed, in terms of its shape and dimensions, as far as appropriate along the lines of the specifications of the ISO 11040-4 standard. A "flange portion" is preferably taken to mean a flange that is formed, in terms of its cross-sectional shape, as far as appropriate along the lines of the specifications of the ISO 8362-1 standard, and on which another object, i.e. a closure element, can be safely attached if necessary. A "standardized syringe" is to be understood as a syringe that complies with the specifications of the aforementioned ISO 11040-4 standard. Similarly, a "standardized vial" is taken to mean a vial that complies with the specifications of the aforementioned ISO 8362-1 standard.

Preferably the cylindrical barrel 23 complies, in terms of its inner diameter, outer diameter and wall thickness, with the relevant specifications of the above-mentioned ISO 11040-4 standard for a suitable specific standardized nominal volume. Said specific standardized nominal volume may correspond to or may be close to, i.e., may slightly differ from, the predetermined filling volume of the container 21, i.e. is a suitable one of the various nominal volumes considered in the ISO 11040-4 standard. In particular, the cylindrical barrel 23 can be formed to meet the barrel diameters d1 and d2 and the barrel wall thickness s1 as indicated in FIG. 1 and table 1 of the ISO 11040-4 standard for a specific standardized nominal volume of a standardized syringe. Depending on the predetermined filling volume, the length of the barrel 23 may conform to the length 11 or total length 1 of a standardized syringe as indicated in FIG. 1 and table B0.1 of ISO 11040-4 standard, or may vary within a range defined by the length 11 and the total length 1 as aforementioned, or may even be different from the specifications of the ISO 11040-4 standard. Generally, the length of the cylindrical barrel 23 is defined and set so that the predetermined filling can be achieved with the inner diameter, outer diameter, and wall thickness adopted from the ISO 11040-4 standard for the specific nominal volume as above explained. If the predetermined filling volume matches a standardized nominal volume of a standardized syringe, the standardized nominal volume can be used as the specific nominal volume, and the cylindrical barrel 23 can be formed to meet the barrel diameters d1 and d2 and the barrel wall thickness s1 as indicated in FIG. 1 and table 1 of the ISO 11040-4 standard for this standardized or specific nominal volume. In this case, the length of the barrel 23 may meet the length 11 as indicated in FIG. 1 and table 1 of the ISO 11040-4 standard for the standardized nominal volume. If the predetermined filling volume differs from any of the nominal volumes set by the ISO 11040-4 standard, any suitable nominal volume close to the predetermined filling volume can be used as the specific nominal volume, and the cylindrical barrel 23 can be formed to meet the barrel diameters d1 and d2 and the barrel wall thickness s1 as indicated in FIG. 1 and table 1 of the ISO 11040-4 standard for this suitable or specific nominal volume. Even if the predetermined filling volume matches a standardized nominal volume of a standardized syringe, however, any other suitable standardized nominal volume can be used as the specific nominal volume, and the cylindrical barrel 23 can be formed to meet the barrel diameters d1 and d2 and the barrel wall thickness s1 as indicated in FIG. 1 and table 1 of the ISO 11040-4 standard for this other standardized or specific nominal volume. For example, if the predetermined filling volume is 1 ml, the cylindrical barrel 23 may meet the outer diameter d1, inner diameter d2, and wall thickness s1 of a 1 ml syringe in a long version, with d1 being 8.15 mm±0.1 mm, d2 being 6.35 mm±0.1 mm, and s1 being approximately 0.9 mm (see ISO 11040-4, tables 1 and B.1 for a nominal volume of 1 ml). In this case, the barrel length may meet the length 11 of the 1 ml syringe in the long version, being 54 mm±0.5 mm, with the specific nominal volume being 1 ml. With the same predetermined filling volume of 1 ml, however, the cylindrical barrel 23 may alternatively meet the outer diameter d1 (=10.85 mm±0.1 mm), inner diameter d2 (=8.65 mm±0.2 mm), and wall thickness s1 (≈1.1 mm) of a 1 ml syringe in a short/standard version (see ISO 11040-4, tables 1 and B.1 for a nominal volume of 1 ml) with the specific nominal volume being 1 ml, or may meet the outer diameter d1 (=6.85 mm±0.1 mm), inner diameter d2 (=4.65 mm±0.1 mm), and wall thickness s1 (≈1.1 mm) of a 0.5 ml syringe (see ISO 11040-4, tables 1 and B.1 for a nominal volume of 0.5 ml) with the specific nominal volume being 0.5 ml. In these alternative cases, the barrel length is appropriately adjusted so as to ensure that the container 21 provides the predetermined filling volume.

Furthermore, the flange portion 26 disposed on top of the cylindrical barrel 23 preferably forms, in a circumferential direction, a continuous circular flange in line with the flange of a conventional vial according to the ISO 8362-1 standard. The flange 26 is also in line with a form B of a finger flange of a standardized syringe (see ISO 11040-4, FIG. 1, Form B). Additionally, the flange portion 26 can be formed to comply, in terms of its cross-sectional shape, with relevant specifications of the above mentioned ISO 8362-1 standard. In particular, the flange portion 26 may meet, in terms of its axial length/height, in terms of its upper inner edge, and/or in terms of its upper end surface, the relevant specifications as indicated in FIGS. 1-3 and table 1 of the ISO 8362-1 standard. Specifically, the axial length/height of the flange 26 may amount to 3.6 mm±0.2 mm, the bevel angle of the upper inner edge may be approximately 45°, and/or the taper angle of the upper end surface of the flange 26 may be 3°±2° (see ISO 8362-1, FIGS. 1 to 3). Adopting the aforementioned length dimensions and angles may be useful in order to enable the flange portion 26 of the container 21 to cooperate with a conventional closure element as specified in the ISO 8362-2 standard. While the above mentioned 3.6 mm±0.2 mm adopted from the ISO 8362-1 standard are preferable, the axial length/height of the flange portion 26 may slightly differ from this standardized dimension as long as the flange portion 26 still meets the following two functions. First, the flange portion 26 must allow for the handling and processing of the container 21 in conventional filling facilities and with conventional technology used for filling and processing of standardized syringes, i.e., the flange portion 26 must meet the function of a finger flange of a standardized syringe (see ISO 11040-4, FIG. 1). A finger flange provides a stop for the user's index and middle fingers while the user's thumb pushes the plunger rod in order to inject the medical or pharmaceutical compound. Second, the design of the flange portion 26 must provide a tight closure of the container 21 by using an appropriate closure element 27, such as a closure element according to the ISO 8362-2 standard of a conventional standardized vial. Furthermore, the flange portion 26 may differ, in terms of its inner diameter, outer diameter and its lower end surface, from the relevant specifications of the ISO 8362-1 standard (see ISO 8362-1, FIG. 1: diameter d4, diameter d2) in order to enable the flange portion 26 to smoothly match the respective barrel dimensions. In particular, the flange portion 26 may have a radially extending flat lower end surface unlike a standardized vial that has a tapered lower surface (see ISO 8362-1, FIGS. 1-3 showing a taper angle of 10°±5°. A flat lower end surface may facilitate the handling of the container 21 in conventional filling facilities and with conventional technology used for filling and processing of standardized syringes. Generally, however, the lower end surface of the flange portion 26 can be formed with a taper angle as it is known from ISO 8362-1 (see FIG. 1-3 showing a taper angle of 10°±5°.

Accordingly, unlike a conventional vial, the container 21 of primary packaging 20 has, at its outer surface, no such neck constriction as shown and specified in the ISO 8362-1 standard (see ISO 8362-1, FIGS. 1-3: diameter d3, height h3). On the other hand, the inner surface of the container 21 can be finished at the upper end, i.e., the upper end section opposite to the flange portion 26, in line with the finish of any appropriate one of vial models A, B, or C of the ISO 8362-1 standard (see ISO 8362-1, FIGS. 1-3).

Furthermore, an inner surface of the container 21, which is in contact with the medical or pharmaceutical compounds stored in the container 21, can be refined by way of subjecting the inner surface to an appropriate surface finishing process and/or coating process. For example, the inner surface can be refined by diverse plasma treatments or siliconized by baked-on or spray siliconization using silicone oil suspensions or silicone oil. Such treatment is known with conventional prefilled syringes in order to enhance the lubrication property of the inner surface of a syringe barrel. It has to be noted, however, that according to the present invention a surface finishing of the inner surface of the container 21 is not restricted to the use of the primary packaging 20 as a syringe, but is open to any type of use of the primary packaging 20 whether it is as a syringe, vial or ampoule, which types of use will be described in the following.

By the configuration according to the present invention, a modular system for assembling a primary packaging 20 is provided that is based on a single type of container 21 that preferably meets, in terms of shape and dimensions of the barrel 23, the relevant specifications of a standardized syringe, and meets, in terms of the cross-sectional shape of the flange portion 26, the relevant specifications of a standardized vial.

The closure element 27 can be any closure element selected from among a group of variants of closure elements, depending on the compound to be stored and/or on the purpose of administration of the compound, and is made of a material suitable for the usage with medical or pharmaceutical compounds 22. Preferably the material of the closure element 27 is an elastomeric material, preferably rubber.

Primary packaging 20 is the combination of a container 21 having a body formed as a cylindrical barrel 23 that complies, as far as appropriate, with the relevant specifications of the above-mentioned ISO 11040-4 standard for a conventional or standardized syringe. Container 21 has a flange portion 26 that complies, in terms of the cross-sectional shape, as far as appropriate with relevant specifications of the above-mentioned ISO 8362-1 standard of a conventional vial. The container 21 is adapted to be filled by standardized or conventional filling facilities and technology used for filling and processing of standardized syringes. Thus, the existing machine capacity of those conventional filling facilities and technology can be used in an advantageous manner. It is noteworthy that the container 21 is permanently closed on one end, unlike the barrel of a conventional standardized syringe, so that the container 21 can also be used as a vial. Furthermore, as mentioned above, unlike a conventional standardized vial the container 21 has no neck constriction between the flange portion 26 and the barrel 23. The continuously circular flange portion 26 is directly joined to the barrel 23.

Another advantage of the present invention originates from the fact that, by meeting the cross-sectional shape of the flange of a standardized vial according to the ISO 8362-1 standard as far as appropriate, the flange portion 26 of the container 21 is manufactured in accordance with the standardized accuracy requirements of a standardized vial according to the ISO 8362-1 standard. Therefore it is possible to use the container 21 with any closure element that is used with a conventional vial. Furthermore, due to the configuration of the flange portion 26 of the container 21, the container 21 fulfills all requirements with respect to impermeability of the ISO 8362-1 standard.

In other words, the combination of the container 21 and the closure element 27 can be used as an alternative to a standardized vial in order to store medical or pharmaceutical compounds 22 and, additionally, can be filled and processed by using conventional filling facilities and technology used for standardized syringes. In this way, the primary packaging 20 has an advantageous double/multiple function.

The flange portion 26 can be formed to function as a finger flange. This means that the flange portion 26 of the container 21 can be formed to function as a finger rest. This configuration allows container 21 to be easily conveyed through a conventional filling facility for standardized syringes. Additionally, the finger flange enables a user easily to grasp the container 21. Of course, the design of the finger-flange may be agreed upon between the customer and manufacturer in compliance with the above-mentioned ISO standards.

Preferably, the closure element 27 is a stopper with a fitting portion adapted to fit tightly into the barrel 23 and a support portion adapted to rest on the flange portion 26. Such a stopper has a "T-shaped" longitudinal cross-section. This configuration of the closure element 27 allows the primary packaging 20 to be used as a conventional vial. The container 21 can be hermetically sealed by the closure element 27 so that medical or pharmaceutical compounds 22 can be stored therein in a well protected manner.

A seal 30, which can also be referred to as an overseal, can be provided that encloses the closure element 27 in a sealing manner, and that engages the flange portion 26 of the container 21. This seal 30 can be used to overseal and secure the closure element 27 in order to maintain the integrity of the sealing of the container 21 under normal conditions of transport, handling and storage during the intended shelf-life of the product. For example, this seal 30 can be made of aluminum.

The seal 30 can be configured as a flip-off seal with an aluminum cap 31 that is placed on the closure element 27 fitted to the container 21, that surrounds the closure element 27 and the flange portion 26 of the container 21, and that engages the flange portion 26 of the container 21. The aluminum cap 31 may have a central opening that is normally closed by a plastics element, e.g., of a flexible or deformable, preferable an elastic, material, and that gives access to the closure element 27 covered by the aluminum cap 31 after removal of the plastics element. The plastics element can be releasably fitted to the aluminum cap 31, e.g., by positive interaction of the plastics element with a circumferential edge of the central opening of the aluminum cap 31, in such a way that it can be flipped off from the aluminum cap 31 to thereby give access, via the central opening of the aluminum cap 31, to the closure element 27 covered by the aluminum cap 31 still being engaged to the container 21. In such flip-off state, a user may extract a medical or pharmaceutical compound from within the container 21 by means of needle extraction system penetrating the closure element 27 via the central opening of the aluminum cap 31.

Figure 2:
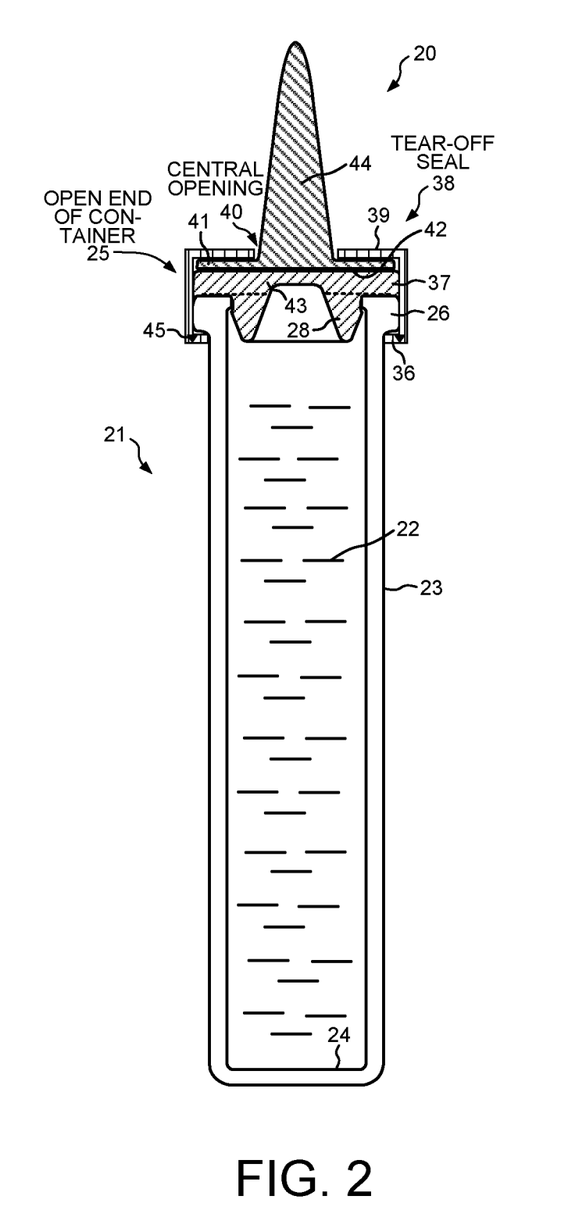
FIG. 2 is a schematized cross-sectional side view of a container with a closure element and a seal according to a another embodiment of the invention.

According to an alternative embodiment, the seal 30 can include a plastics element 33 having a flat lower surface that rests on the above-mentioned support portion of the closure element 27. The seal 30 also has an aluminum cap 31 that surrounds the plastics element 33 and that has a central opening giving access to the plastics element 33 covered by the aluminum cap 31.

The plastics element 33 of the seal 30 can include a gripping portion 44 that penetrates the central opening of the aluminum cap 39 to extend axially outwards. The gripping portion 44 can be an integral part of the plastics element 33 or can be securely fitted to the plastics element. By this configuration, the gripping portion 44 can be easily grasped by a user in order to remove, along with the plastics element 33, the aluminum cap 39 and preferably the closure element 27 from the container 21.

Figure 3:
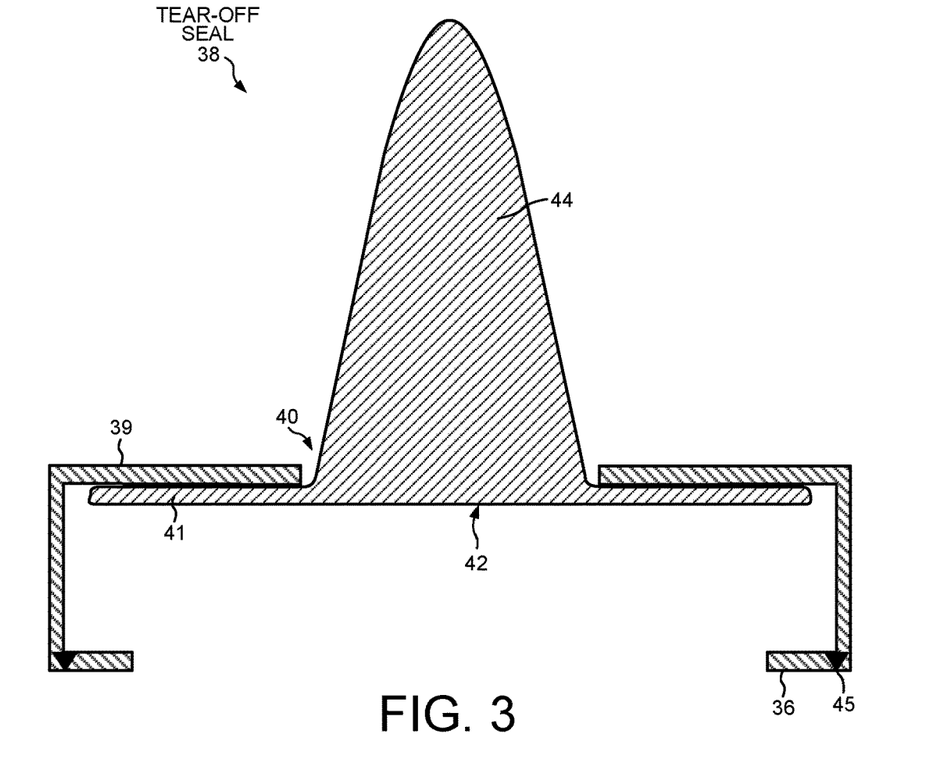
FIG. 3 is an enlarged, schematized cross-sectional side view of the seal of FIG. 2.

The aluminum cap 39 can include a predetermined breaking point 45 at a portion that engages the flange portion 26 of the container 21. By equipping the aluminum cap 39 with a circumferentially extending breaking point 45, removal of the plastics element 33 and part of the closure element 27 is facilitated by snapping or folding the gripping element 44. For example, the aluminum cap 39 can be tightly fitted, e.g. by friction, to the closure element 27 so that removing the aluminum cap 39 causes a removal of the whole closure element 27 by friction along with the aluminum cap.

The closure element can also be a cylindrical plunger stopper comprising a fitting portion adapted to fit tightly into the barrel 23 of the container 21.

Figure 5:
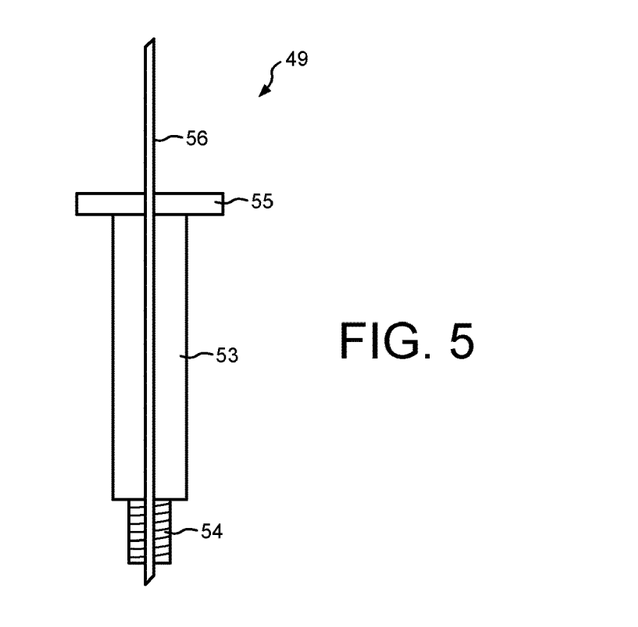
FIG. 5 is a schematized cross-sectional side view of a needle extraction system.

Another improvement can be achieved by providing an optional needle extraction system 49 for removal of the medical or pharmaceutical compound, wherein the needle extraction system 49 is adapted to cooperate with the plunger stopper. It is remarkable that in this case the needle extraction system 49, when cooperating with the plunger stopper, extends outwards from the open second end 25 of the container 21. For a cooperation of the needle extraction with the closure element formed as a plunger stopper, the needle extraction system 49 and the plunger stopper can be provided with appropriate engaging or attachment means that are adapted to fit to each other. By this configuration, the primary packaging 20 can be used as a vial, as an ampoule or as a syringe, while being still producible by a conventional filling facility used for standardized syringes. The filling volume of the barrel 23 can be even larger than in the case of a standard syringe because no needle extends from the permanently closed first end 24 of the container 21. Consequently, in this case the barrel 23 can have a length that is larger compared to a standard syringe, while still being producible by a conventional filling facility.

The needle extraction system 49 can comprise a plunger rod element that is releasably attachable to the plunger stopper by a snap fit connection or, alternatively, by a screw fit connection. In this way, the primary packaging 20 can be easily converted to a syringe. Contrary to a conventional prefilled syringe, however, the primary packaging 20 when used as a syringe is both filled and extracted via the open second end 25 of the container 21, i.e., at the same end side of the container 21.

The plunger rod element can have a finger flange in order to facilitate the removal of the medical or pharmaceutical compounds 22 stored in the container 21. A cannula 56 can be fixed to the plunger rod element.

A seal can be provided that at least partially encloses the closure element in a sealing manner and that can also engage the flange portion 26 of the container 21. Especially if the closure element is made of rubber, such a seal can be used as an overseal to secure the closure element to the container 21 in order to maintain the integrity of the sealing under normal conditions of transport, handling and storage during an intended shelf-life of the product.

The present invention additionally relates to a method for assembling a primary packaging 20 for storage and/or administration of medical or pharmaceutical compounds 22. The method comprises the following steps:

Providing a container 21 having a predetermined filling volume for receiving a medical or pharmaceutical compound such that the container 21 is permanently closed at a first end 24 and has an integrally formed, circumferential flange portion 26 at an open second end 25. The container 21 has a cylindrical barrel 23 that extends between the first end 24 and the flange portion 26.

Selecting a closure element from among a group of variants of closure elements, depending on the compound to be stored and/or on the purpose of administration of the compound. The closure element is adapted to fit tightly onto the flange portion 26 and/or to fit tightly into the barrel 23 for sealing the open second end 25 of the container 21.

Providing a seal that at least partially encloses the selected closure element in a sealing manner and that engages the flange portion 26 of the container 21.

Optionally providing a needle extraction system for removal of the medical or pharmaceutical compound such that the needle extraction system is adapted to cooperate with the plunger stopper.

The container 21 includes the barrel 23 and flange portion 26. The closure element, the seal and the optionally provided needle extraction system are combined with the container 21 to form the primary packaging 20.

As for the container 21 used in the method for assembling the primary packaging 20 for storage and/or administration of medical or pharmaceutical compounds, the provided container 21 is selected, in terms of the barrel 23, depending on the predetermined filling volume and, in terms of the flange portion 26, depending on the desired form of administration of the chemical or pharmaceutical compound stored in the container 21. The inner diameter, outer diameter and wall thickness of the cylindrical barrel 23 of the container 21 are set so as to meet the relevant specifications of the ISO 11040-4 standard for a suitable one of the standardized nominal volumes of a standardized syringe. The suitable one of the standardized nominal volumes may correspond to or can be close to the predetermined filling volume of the container 21. Depending on the predetermined filling volume and the inner diameter, outer diameter and wall thickness of the barrel 23, the length of the barrel 23 can be set so as ensure that the container 21 provides the predetermined filling volume. Furthermore, the flange portion 26 can be formed to comply, in terms of its cross-sectional shape, with relevant specifications of the above-mentioned ISO 8362-1 standard, as above specified.

The primary packaging 20 can be assembled by using a modular system in which the individual components, i.e., the container 21, the various closure elements, the various seals, etc., are approved for usage with pharmaceuticals and in which the individual components are easily exchangeable. Here, the primary packaging 20 can be used either as a vial, as an ampoule or as a syringe, while still being producible by a conventional filling facility for standardized syringes. It is notable that the modular system for assembling a primary packaging 20 includes a single type of container 21 that is suitable for various closure elements and optionally, where necessary, a needle extraction system. Regarding the needle extraction system, it is also noteworthy that the end side of removal of the medical or pharmaceutical compound from the container 21 is the very same end side as the end side of filling the container 21. The closure element can be selected from a group of variants of closure elements, including a stopper and a cylindrical plunger stopper. The stopper includes a fitting portion adapted to fit tightly into the barrel 23 and a support portion adapted to rest on the flange portion 26. The cylindrical plunger stopper includes a fitting portion adapted to fit tightly into the barrel 23 of the container 21 and adapted to cooperate with an optionally provided needle extraction system.

FIG. 1 shows a cross-sectional side view of an embodiment of a primary packaging 20 that serves for storage and/or administration of any medical or pharmaceutical compounds. The primary packaging 20 is normally in direct contact with these compounds. The primary packaging 20 includes a container 21 made of glass or any appropriate plastics material and that has a defined filling volume for receiving the medical or pharmaceutical compounds 22. The container 21 has a cylindrical barrel 23 and is permanently closed at a first end 24 that forms the bottom of the container 21. Furthermore, the container 21 has an open second end 25 that forms the top of the container 21. At the open second end 25, an integrally formed, circumferential flange portion 26 is provided that extends radially outwardly from the barrel 23. This means that the barrel 23 extends between the closed first end 24 and the flange portion 26 in a cylindrical shape.

In one embodiment, the container 21 has an exemplary predetermined filling volume of 1.9 ml. For this purpose, the barrel 23 of the container 21 has an outer diameter of 8.15 mm and an inner diameter of 6.35 mm, as specified by the ISO 11040-4 standard. ISO standard 11040-4 (FIG. 1 and tables 1 and B.1 for dimensions d1, d2) also defines the so-called long version of a standardized syringe having a nominal volume of only 1 ml. Due to the fact that the first end 24 of the container 21 is permanently closed instead of having a head-shaped end known from a conventional standardized syringe for holding a needle cannula (see ISO 11040-4, figures A.1 to A.3 showing various head designs), the total length of the filling volume of the barrel 23, in this embodiment, can be approximately 64 mm compared to the total length of the filling volume of the barrel of the aforementioned long version of the conventional standardized syringe, which is only 54 mm (cf. ISO 11040-4, Table 1, 11 for a nominal volume of 1 ml). The conventional standardized syringe is 54 mm long because it needs an unspecified additional amount of length corresponding to the length of the head design of a conventional standardized syringe (see ISO 11040-4, figures A.1 to A.3 showing various head designs) and a rubber needle shield placed on the head design. Accordingly, due to the increased length of the barrel 23, the container 21 may provide a filling volume of 1.9 ml while still having the inner diameter and outer diameter of a standardized syringe with a nominal volume of only 1 ml. In analogy to this one example, however, other prefilled syringe dimensions as described in the ISO 11040-4 standard can also be extended.

The flange portion 26 of the container 21 is manufactured, as far as appropriate, according to the cross-sectional shape and the standardized manufacturing accuracy of a flange of a standardized vial according to the ISO 8362-1 standard. In particular, the flange portion 26 put on top of the cylindrical barrel 23 forms, in a circumferential direction, a continuous circular flange in line with the flange of a conventional vial according to the ISO 8362-1 standard. The flange also conforms to a form B of a finger flange of a standardized syringe (see ISO 11040-4, FIG. 1, Form B). Additionally, the flange portion 26 is formed in order to comply with the relevant specifications as indicated in FIGS. 1-3 and table 1 of the ISO 8362-1 standard, in terms of its cross-sectional shape, its axial length/height, its upper inner edge, and its upper end surface. Specifically, the axial length/height of the flange portion 26 amounts to 3.6±0.2 mm, the beveled angle of the upper inner edge is approximately 45°, and the taper angle of the upper end surface of the flange is 3°±2° (see ISO 8362-1, FIGS. 1-3).

Furthermore, in the embodiment shown in FIG. 1, the flange portion 26 has a tapered lower end surface with a taper angle of 10°±5° similar to a standardized vial (see ISO 8362-1, FIGS. 1-3). On the other hand, the flange portion 26 differs, in terms of its inner diameter and outer diameter, from the relevant specifications of the ISO 8362-1 standard because it is formed to smoothly match the respective barrel dimensions as shown in FIG. 1. Instead of the tapered lower end surface seen in FIG. 1, the flange portion may have a radially extending flat lower end surface. Unlike a conventional vial, however, the container 21 of the primary packaging according to the present invention has no neck constriction as is specified in the ISO 8362-1 standard (see ISO 8362-1, FIG. 1: d3, h3). But the container 21 can be finished on the inner side as described in the aforementioned standard (see ISO 8362-1, FIGS. 1-3: neck finish with or without blow back according to Models A, B, C).

As further shown in FIG. 1, the primary packaging 20 also includes a suitable closure element 27 that is adapted to fit tightly onto the flange portion 26 and to fit tightly into the barrel 23 through the open second end 24 of the container 21. In this embodiment, the closure element 27 is a stopper that is made of rubber. The closure element 27 has a fitting portion 28 adapted to fit tightly into the barrel 23 and a support portion 29 adapted to rest on the flange portion 26 in a sealing manner. The container 21 is sealed by the support portion 29 being pressed against the upper surface of the flange portion 26. The closure element 27 can conform to the cross-sectional shape and relevant dimensions of a stopper that is standardized in the ISO 8362-2 standard, or its dimensions are adapted to more convenient dimensions.

The primary packaging 20 also includes a flip-off type seal 30 that has an aluminum cap 31. The aluminum cap 31 is placed over the closure element 27 fitted to the container 21 and surrounds both the closure element 27 and the flange portion 26 of the container 21. The aluminum cap 31 wraps around and engages the flange portion 26 of the container 21. The aluminum cap 31 has a central opening 32 that is normally, i.e., during storage, transport, etc., closed by a plastics element 33. The central opening 32 of the aluminum cap 31 allows access to the closure element 27 after removal of the plastics element 33.

The plastics element 33 has a flat lower surface 34 that rests on the aluminum cap 31. The plastics element 33 is made from an flexible, in this embodiment elastic, material and is releasably fitted to the aluminum cap 31 by positive interaction with a circumferential edge of the central opening 32 of the aluminum cap 31 in such a way that it can be flipped off from the aluminum cap 31 to thereby give access, via the central opening 32, to the closure element 27 located below the aluminum cap 31 still being engaged to the container 21. In such a flip-off state, a user can extract a medical or pharmaceutical compound from within the container 21 by means of a needle extraction system that penetrates a weak membrane portion 35 of the closure element 27, via the central opening 32 of the aluminum cap 31. The seal 30 includes an engaging portion 36 that tightly encloses the closure element 27 in a sealing manner and engages the flange portion 26 of the container 21. As shown in FIG. 1, the seal 30 functions as an overseal to secure the closure element 27 to the container 21. In this way, the seal 30 keeps the container 21 and closure element 27 in a sterile condition. By this configuration, the primary packaging 20 functions as a conventional vial.

FIG. 2 is a cross-sectional side view of another variant of a closure element 37 that is fitted to the container 21 of FIG. 1 instead of the closure element 27. In this embodiment, a tear-off type seal 38 includes an aluminum cap 39 with a central opening 40 and a plastics element 41 having a flat lower surface 42 adapted to rest on a support portion 43 of the closure element 37. Furthermore, the seal 38 includes a gripping portion 44 having an outwardly extending form. In particular, the gripping portion 44 penetrates outwardly through the central opening 40 of the aluminum cap 39, as it is seen in FIG. 2, so that the gripping portion 44 can be easily grasped by the user. In this variant of closure element 37, the gripping portion 44 is integrally formed with the plastics element 41. Alternatively, the gripping portion 44 can be formed separately from and then securely fitted to the plastics element 41. A circumferentially extending, predetermined breaking point 45 (cf. FIG. 3) is disposed at the engaging portion 36 of the aluminum cap 39 and engages the flange portion 26 of the container 21. The lifting, slanting or snapping of the gripping portion 44 causes the major part of the aluminum cap 39 as well as the closure element 37 to be removed from the container 21. To this end, the aluminum cap 39 and the closure element 37 are in tight frictional contact with each other. In this way, the primary packaging 20 functions and can be used as an ampoule.

FIG. 3 shows an enlarged, schematized cross-sectional side view of the aluminum cap 39 and the plastics element 41 that fit over the closure element 37. In particular, the position of the predetermined breaking point 45 at the engaging portion 36 of the aluminum cap 39 can be clearly seen.

Figure 4:
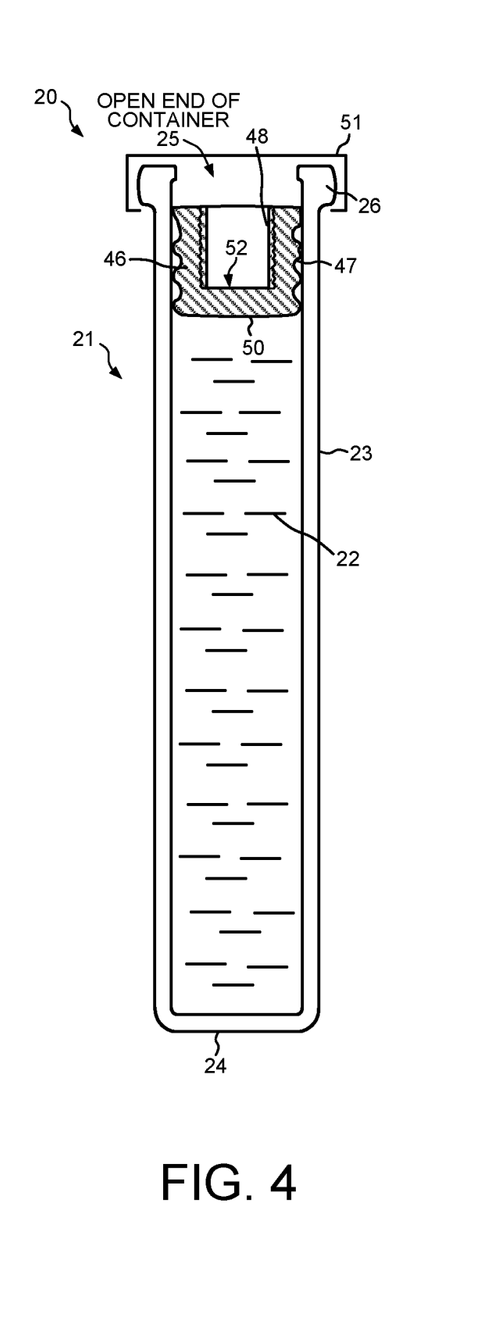
FIG. 4 is a schematized cross-sectional side view of a container with a closure element according to yet another embodiment of the invention.

FIG. 4 shows a further embodiment of a primary packaging in a schematized sectional side view. In this embodiment, a container 21 of the same type as described above with reference to FIGS. 1-2 is plugged at its open first end 25 by another variant of a closure element that is formed as a cylindrical plunger stopper 46. This plunger stopper 46 has a fitting portion 47 adapted to fit tightly into the barrel 23 of the container 21. On its top, which means on the side facing to the open second end 25 of the barrel 23, the plunger stopper 46 has an attachment means 48 which, in this embodiment, is formed as a female threaded hole according to ISO 11040 no. 4.1 b). Attachment means 48 forms a screw connection for a needle extraction system 49 shown in FIG. 5. On its bottom side, which means on the side facing the closed first end 24, the plunger stopper 46 has a thin bottom portion 50 that is adapted to be pierceable by a conventional cannula or a hollow needle as shown in FIG. 5. In this embodiment, the closure element 46 is oversealed by a seal 51, which may correspond in its structure to the seal 30 shown in FIG. 1. The seal 51 is appropriate in particular if the primary packaging 20 is to be stored, transported, sold, etc. as an intermediate product, i.e., without the needle extraction system 49 being attached to the closure element 46. In case the primary packaging is to be stored, transported, sold, etc. as final product, i.e., with the needle extraction system 49 being attached to the closure element 46, however, the primary packaging 20 does not include the seal 51, so that the seal 51 can be provided only if appropriate. In this latter case, if the primary packaging 20 is assembled as a final product, the needle extraction system 49 can be partly or loosely attached to the closure element 46 so that a weak membrane portion 52 at the bottom of the attachment means 48 of the closure element 46 is not yet penetrated. The needle extraction system 49 is fully or tightly attached to the closure element 46 by the user in order to penetrate the weak membrane portion 52 and the thin bottom portion 50 of the closure element 46 only at the time of removal of the medical or pharmaceutical compound from within the container 21.

FIG. 5 shows a schematized cross-sectional side view of the needle extraction system 49 for removal of the medical or pharmaceutical compounds 22 from within the container 21. The needle extraction system 49 can be provided as an optional component of the primary packaging 20 and includes a cylindrical plunger rod element 53 that has an outer diameter which is smaller than the inner diameter of the barrel 23. The plunger rod element 53 has a length that preferably corresponds to the length of the barrel 23. Furthermore, the plunger rod element 53 further has an attachment means 54 disposed at a first axial end, which is formed as a male threaded portion of plastic for making a screw connection with the closure element 46. By such attachment means 54, the plunger rod element 53 is releasably attachable to the attachment means 48 of the plunger stopper 46. At the second axial end of the plunger rod element 53, a finger flange 55 extends radially outwards and is formed so that it can be easily grasped by a user.

The plunger rod element 53 also includes a cannula 56 that extends axially through the entire plunger rod element 53. That means that the cannula 56 protrudes through both axial ends of the plunger rod element 53. In this embodiment, the cannula 56 is formed as a hollow needle that is securely fixed to the plunger element 53. Alternatively, however, the cannula 56 can be integrally formed with the plunger rod element 53. Furthermore, the cannula 56 is adapted to pierce the thin bottom portion 50 of the plunger stopper 46. When the needle extraction system 49 is attached to the plunger stopper 46 and is moved in an axial direction towards the first end 24 of the barrel 23, the medical or pharmaceutical compounds 22 can be removed from the container 21. In order to reduce the amount of compound 22 remaining in the container after having fully operated the needle extraction system 49, the protrusion of the cannula 56 from a lower side of the plunger rod element 53 is minimized as short as possible. In this way, the primary packaging functions as a (pre-filled) syringe.

Figure 6:
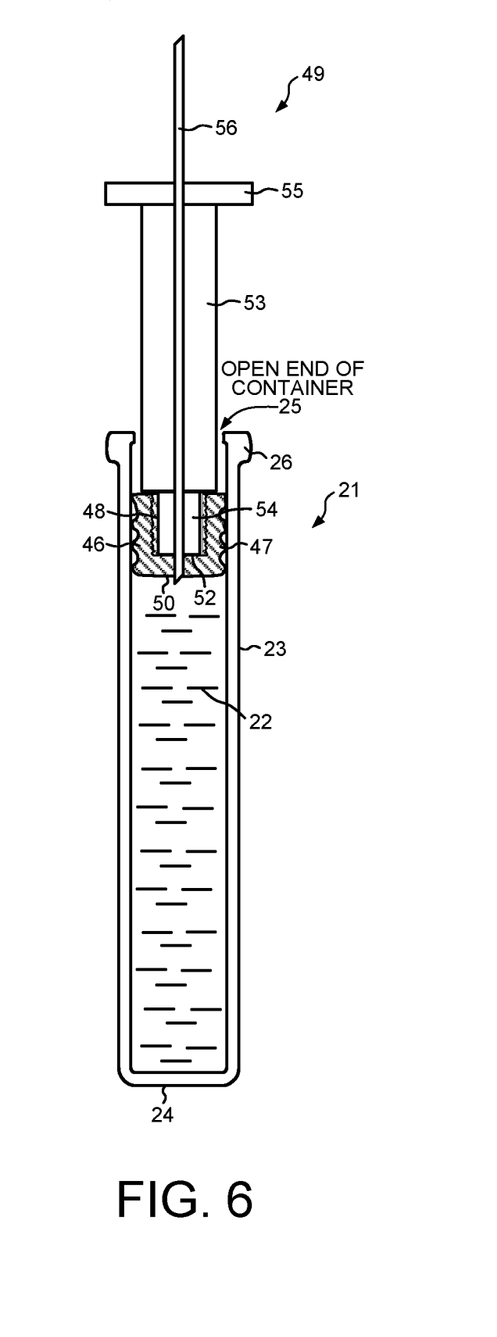
FIG. 6 is a schematized cross-sectional side view of a container with a closure element and the needle extraction system of FIG. 5 attached to the closure element.

FIG. 6 is a schematized cross-sectional side view of the primary packaging 20 when the needle extraction system 49 is fitted to the plunger stopper 46. Seal 51, if present, must first be removed before the needle extraction system 49 is attached to the plunger stopper 46.

Figure 7:
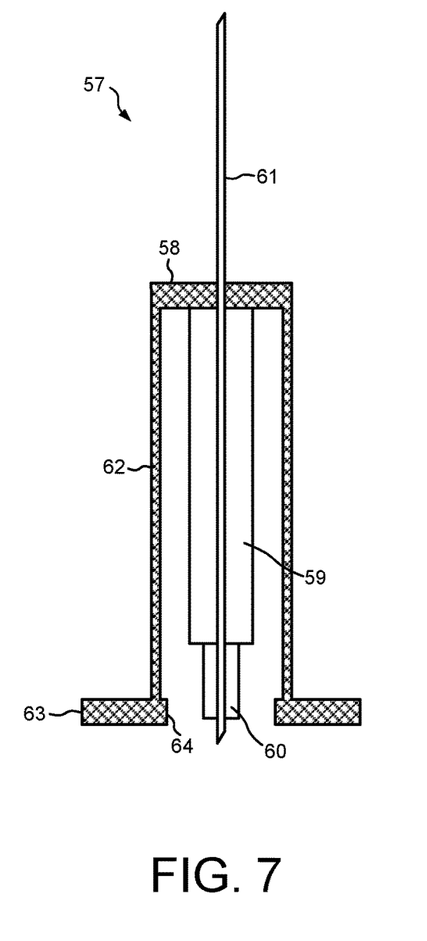
FIG. 7 is a schematized cross-sectional side view of a needle extraction system according to another embodiment of the invention.

In FIG. 7 is a schematized cross-sectional side view of another embodiment of the needle extraction system 57. The needle extraction system 57 includes a cylindrical tube section 62 with an open end and an abutting portion 58 at the opposite closed end. The radially extended abutting portion 58 is integrally formed with a first axial end of a plunger rod element 59. Alternatively, the abutting portion 58 can be releasably attached to the first axial end of the plunger rod element 59. Thus, the plunger rod element 59 is attached inside the tube section 62 to the abutting portion 58. The plunger rod element 59 has an outer diameter that is smaller than the inner diameter of the barrel 23. The tube section 62 has an inner diameter that is larger than the outer diameter of the barrel 23. The plunger rod element 59 slides inside the barrel 23 while the tube section 62 slides down around the outside of the barrel 23. The plunger rod element 59 includes an attachment means 60 that corresponds to the attachment means 54 as described with reference to FIGS. 5-6. The needle extraction system 57 also includes a cannula 61 that extends through the entire plunger rod element 59.

The cylindrical tube section 62 of the needle extraction system 57 of FIG. 7 extends substantially coaxially with the plunger rod element 59 from the abutting portion 58 in the direction of the second axial end of the plunger rod element 59 facing away from its first axial end. The tube section 62 has a radially outwardly extending finger flange 63 disposed at its open end adjacent to the second axial end of the plunger rod element 59. The finger flange 63 can easily be grasped by a user. The finger flange 63 has a radially inwardly extending projection 64 that is configured to slide along the outer surface of the container 21. To assemble the needle extraction system 57 to the container 21, the tube section 62 can be, within limits, elastically deformable such that its end portion including the finger flange 63 is slightly radially expandable.

In the configuration shown in FIG. 7, the plunger rod element 59 can be placed in the barrel 23 of the container 21. The lengths of the plunger rod element 59 and of the tube section 62 are adapted to the inner length of the barrel 23 so that an entire stroke of the plunger rod element 59 or the full distance of the tube section 62, respectively, corresponds to the inner length or depth of the barrel 23.

Figure 8:
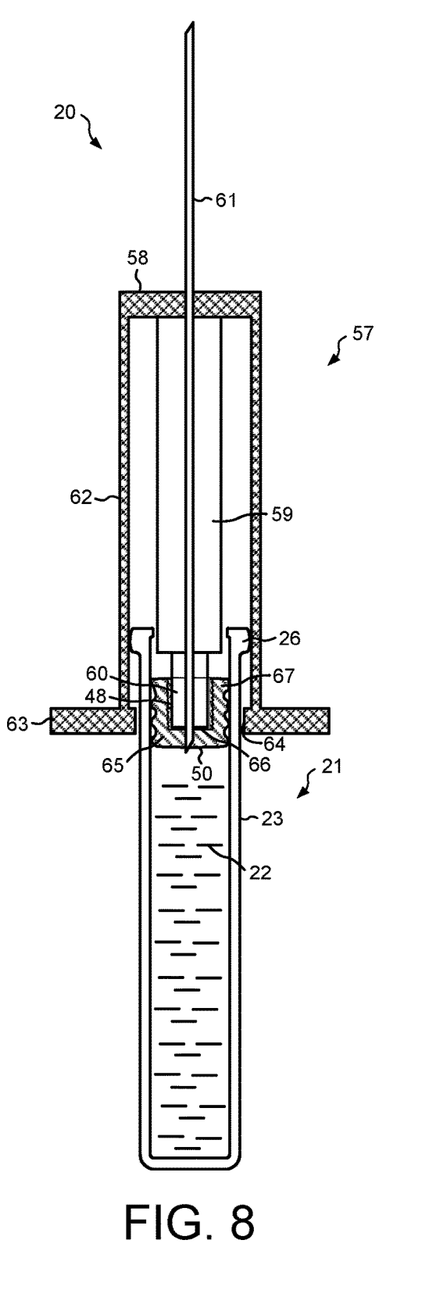
FIG. 8 is a schematized cross-sectional side view of a container with a closure element and the needle extraction system of FIG. 7 attached to the closure element.

FIG. 8 is a schematized cross-sectional side view of the primary packaging 20 with the needle extraction system 57 fitted to a plunger stopper 65. The plunger stopper 65 corresponds to the plunger stopper 46 described above. FIG. 8 shows that the lengths of the plunger rod element 59 and of the tube section 62 correspond to the length of the barrel 23. With the projection 64 of the tube section 62, the needle extraction system 57 can be used as a disposable syringe.

The aforementioned configuration provides a modular system for assembling a primary packaging that is based on a single type of container 21 that preferably meets, in terms of the cross-sectional shape and dimensions of the barrel 23, the relevant specifications of the barrel of a standardized syringe and meets, in terms of the cross-sectional shape at least with respect to its upper end, the relevant specifications of the flange of a standardized vial. In particular, the barrel 23 is preferably formed to comply with the ISO 11040-4 standard in terms of the barrel diameters $d1$, $d2$, and $d5$ and the barrel wall thickness $s1$ as indicated in FIG. 1 and tables 1 and B.1, respectively, of the ISO 11040-4 standard. Furthermore, the flange portion 26 is preferably formed to comply with the ISO 8362-1 standard specifications at least in terms of the upper end cross-sectional shape. On the other hand, in terms of the inner diameter and outer diameter, the flange portion 26 may differ from the respective specifications of the ISO 8362-1 standard and can be designed so as to match the barrel dimensions. Thus, the container 21 is formed by the barrel 23 and a flange portion 26 matching the barrel. Accordingly, the container 21 does not have any such neck constriction as does a conventional vial.

Furthermore, the closure element is selected from a group of variants of closure elements according to the user's needs and desired type of administration of the medical or pharmaceutical compound stored in the container. The group of variants of closure elements includes a stopper with a fitting portion adapted to fit tightly into the barrel and a support portion adapted to rest on the flange portion (cf. FIG. 1), and a cylindrical plunger stopper with a fitting portion adapted to fit tightly into the barrel of the container and adapted to cooperate with an optionally provided needle extraction system (see FIG. 2). Other types of closure elements can be added to the group of variants.

The primary packaging 20 according to the present invention can be assembled by using a modular system. First, the container 21 for receiving the medical or pharmaceutical compounds 22 is provided. The container 21 functions as a unified, multifunctional type of container for any specific use of the primary packaging 20, such as for use as a vial, a syringe or an ampoule. Furthermore, a suitable closure element is selected from among a group of variants of closure elements, depending on the compound to be stored and/or on the purpose of administration of the compound. The group of variants of closure elements includes the closure element 27 according to FIG. 1 which is formed as a stopper, the closure element 37 according to FIG. 2, and the closure element formed as a plunger stopper 46 or 65 according to FIG. 4, 6 or 8. In order to overseal the selected closure element after having filled the container 21, the seal 30, 38 is attached to the container 21. If the primary packaging 20 is to be used as a syringe, the needle extraction 49 or 57 is attached to the primary packaging 20. Thus, the primary packaging 20 can be assembled depending on the compound to be stored and/or on the purpose of administration of the compound. As above mentioned, the needle extraction system 49 or 57 can be provided to the primary packaging 20 as a separate accessory component or can be partially or loosely attached to the closure element 46 or 65 without penetrating a weak membrane portion 52, 66 or the thin bottom portion 50 of the closure element 46, 65.

Based on the illustrated embodiments, the primary packaging 20 can be modified in many ways. For example, the above described screw-fit attachment means 47, 54 of FIG. 6 or 67, 60 of FIG. 8 can be replaced by a conventional snap fit connection according to ISO 11040-5 no. 4.1 a).

Furthermore, in any of the above described embodiments and in the assembling method, an inner surface of the container 21, which is in contact with the medical or pharmaceutical compound stored in the container 21, can be refined by way of subjecting the inner surface to an appropriate surface finishing process and/or coating process. For example, the inner surface can be treated by diverse plasma treatments or siliconized by baked-on or spray siliconization using silicone oil suspensions or silicone oil. Such treatment is known with conventional prefilled syringes in order to enhance the lubrication property of the inner surface of a syringe barrel or in vials to reduce the extractable volume losses. It has to be noted, however, that according to the present invention a surface finishing of the inner surface of the container is not restricted to the use of the primary packaging as a syringe, but is open to any type of use of the primary packaging whether it is as a syringe, vial or ampoule, which types of use will be described in the following.

The present invention relates to a primary packaging for storage and/or administration of medical or pharmaceutical compounds. The primary packaging includes a container that has a predetermined filling volume for receiving a medical or pharmaceutical compound. The container is permanently closed at a first end and has an integrally formed, circumferential flange portion at an open second end. The container has a cylindrical barrel that extends between the first end and the flange portion. The barrel preferably has an inner diameter and outer diameter corresponding to that of a standardized syringe for a nominal volume of the standardized syringe corresponding to or being close to the predetermined filling volume. Furthermore, a cross-sectional shape of the flange portion preferably corresponds to the cross-sectional shape of a flange of a standardized vial. The primary packaging also includes a closure element that is adapted to fit tightly on the flange portion and/or into the barrel for sealing the open second end of the container.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A device comprising:
   a container with a cylindrical barrel, a permanently closed first end and an open second end, wherein a circumferential flange is integrally formed at the open second end and has an outer diameter that is larger than an outer diameter of the cylindrical barrel, and wherein the circumferential flange has a cross sectional shape that has a flat upper end surface and a flat lower end surface;
   a closure element that fits tightly into the open second end of the container; and
   a needle extraction system having a plunger rod and a cylindrical tube section, wherein a first end of the plunger rod fits into the closure element, wherein the cylindrical tube section has an inner diameter that is larger than the outer diameter of the cylindrical barrel and has a radially outwardly extending finger flange, wherein the finger flange has a radially inwardly extending projection that slides along an outer surface of the cylindrical barrel, wherein the radially inwardly extending projection has a first flat upper end surface oriented parallel to a cross-sectional plane of the cylindrical tube section, and wherein the circumferential flange slides along an inner surface of the cylindrical tube section.

2. The device of claim 1, wherein the circumferential flange slides along the inner surface of the cylindrical tube section from the radially inwardly extending projection to a closed end of the cylindrical tube section.

3. The device of claim 1, wherein the flat upper end surface of the circumferential flange of the container has a taper angle between one and five degrees relative to a cross-sectional plane of the cylindrical barrel.

4. The device of claim 1, wherein the radially inwardly extending projection of the finger flange has a second flat lower end surface.

5. The device of claim 1, wherein the cylindrical barrel has dimensions that comply with specifications of ISO standard 11040-4 for a prefilled syringe barrel.

6. The device of claim 1, wherein the circumferential flange has dimensions that comply with specifications of ISO standard 8362-1 for an injection vial flange.

7. The device of claim 1, wherein the closure element has dimensions that comply with specifications of ISO standard 8362-2 for a closure of an injection vial.

8. The device of claim 1, wherein the radially outwardly extending finger flange and the radially inwardly extending projection extend at right angles from the cylindrical tube section.

9. A device comprising:
   a container with a cylindrical barrel, a permanently closed first end and an open second end, wherein a circumferential flange is integrally formed at the open second end and has an outer diameter that is larger than an outer diameter of the cylindrical barrel, wherein the circumferential flange has a cross sectional shape that has a flat upper end surface and a flat lower end surface, and wherein the cylindrical barrel has an inner surface that has been siliconized using silicone oil;
   a closure element that is fitted tightly into the open second end of the container; and
   a needle extraction system with a plunger rod and a cylindrical tube section, wherein a first end of the plunger rod fits into the closure element, wherein the cylindrical tube section has an inner diameter that is larger than the outer diameter of the cylindrical barrel, wherein the cylindrical tube section has a radially outwardly extending finger flange disposed at its open end adjacent to an end of the plunger rod inside the cylindrical tube section, wherein the finger flange has a radially inwardly extending projection that slides along an outer surface of the cylindrical barrel, and wherein the radially inwardly extending projection has a first flat upper end surface oriented parallel to a cross-sectional plane of the cylindrical tube section.

10. The device of claim 9, wherein the circumferential flange slides along an inner surface of the cylindrical tube section.

11. The device of claim 9, wherein the flat upper end surface of the circumferential flange has a taper angle between one and five degrees relative to a cross-sectional plane of the cylindrical barrel.

12. The device of claim 9, wherein the radially inwardly extending projection of the finger flange has a second flat lower end surface.

13. The device of claim 9, wherein the first end of the plunger rod can be screwed into the closure element.

14. A method comprising:

fitting a plunger stopper tightly into a first open end of a container, wherein the container has a cylindrical barrel, a permanently closed second end and a circumferential flange formed around the first open end, wherein the circumferential flange has an outer diameter that is larger than an outer diameter of the cylindrical barrel, wherein the circumferential flange portion has a cross-sectional shape that has a flat upper end surface and a flat lower end surface, and wherein the plunger stopper has a female threaded hole with a thin bottom portion between the female threaded hole and a bottom side of the plunger stopper; and partially screwing a male threaded end of a plunger rod into the female threaded hole, wherein a top axial end of the plunger rod is attached inside a tube section, wherein the tube section has an inner diameter that is larger than the outer diameter of the cylindrical barrel, wherein the tube section has a radially inwardly extending projection disposed at its open end that slides along an outer surface of the cylindrical barrel, wherein the radially inwardly extending projection has a first flat upper end surface oriented parallel to a cross-sectional plane of the tube section, wherein the plunger rod has an outer diameter that is smaller than an inner diameter of the cylindrical barrel, wherein a cannula extends axially through the plunger rod and protrudes through both the male threaded end and the top axial end of the plunger rod, and wherein the thin bottom portion is not penetrated by the cannula that protrudes from the male threaded end of the plunger rod when the male threaded end is partially screwed into the female threaded hole.

15. The method of claim 14, wherein the plunger rod fits inside the cylindrical barrel while the tube section fits around the outer surface of the cylindrical barrel.

16. The method of claim 14, further comprising:

pushing the plunger rod into the cylindrical barrel, wherein the radially inwardly extending projection slides along the outer surface of the cylindrical barrel as the plunger rod is pushed into the cylindrical barrel.

17. The method of claim 14, wherein the circumferential flange has dimensions that comply with specifications of ISO standard 8362-1 for an injection vial flange.

18. The method of claim 14, wherein the cylindrical barrel has dimensions that comply with specifications of ISO standard 11040-4 standard for a prefilled syringe barrel.

19. The method of claim 14, wherein the plunger stopper has dimensions that comply with specifications of ISO standard 8362-2 for a closure of an injection vial.

20. The method of claim 14, wherein the container is a vial that complies with ISO standard 8362 for a vial, and wherein the cylindrical barrel has an inner surface that has been siliconized using silicone oil.

* * * * *